United States Patent [19]

Tokarz

[11] 4,412,825
[45] Nov. 1, 1983

[54] MEDICAL ENTRY CONNECTOR FOR TEETH BEARING ANIMALS

[76] Inventor: Richard D. Tokarz, 4188 Laurel Dr., West Richland, Wash. 99352

[21] Appl. No.: 303,010

[22] Filed: Sep. 17, 1981

[51] Int. Cl.³ ............................................ A61C 00/00
[52] U.S. Cl. .................................... 433/229; 128/1 R
[58] Field of Search .................... 128/1 R, 1 C; 3/1.1; 433/215, 229, 167, 81, 224

[56] References Cited

U.S. PATENT DOCUMENTS

| | | | |
|---|---|---|---|
| 2,436,623 | 2/1948 | Van Zile | 433/81 |
| 3,156,787 | 11/1964 | Puharich et al. | 128/1 R |
| 3,674,013 | 7/1972 | Polanyi | 126/6 |
| 3,863,622 | 2/1975 | Buuck | 128/1 R |

*Primary Examiner*—Robert Peshock

*Attorney, Agent, or Firm*—Wells, St. John & Roberts

[57] ABSTRACT

In a subcutaneous body entry communication device, the device including a first and second communication pathway means for operably interconnecting an external device to an internal body location. The first communication pathway means being implanted in an animal's tooth; the second communication pathway means being implanted in the animal's jaw and being operably connected between the first communication pathway means and the internal body location.

The method for implanting the first communication pathway device involving excavating an aperture in the tooth; the means for implanting the second communication pathway device involving surgical procedures. The body entry communication device being configurable as an electrical, a light or a fluid conductor.

30 Claims, 6 Drawing Figures

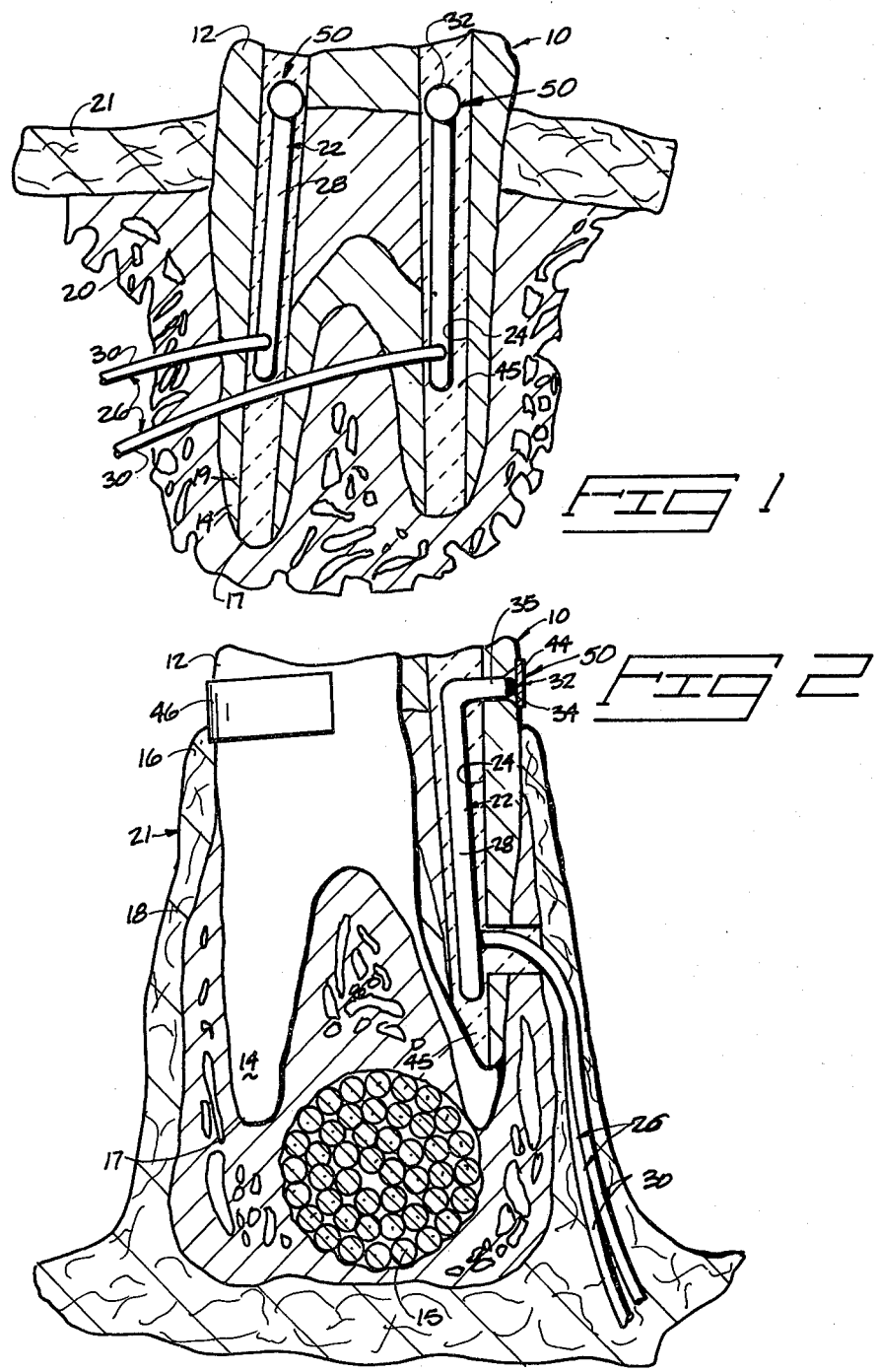

1

MEDICAL ENTRY CONNECTOR FOR TEETH BEARING ANIMALS

BACKGROUND ART

Solving the problem of extending electrical, hydraulic or any other type of communicating means through the skin of animals or humans is difficult. Communicating means brought through the skin are a natural location for infection; they are subject to being dislodged during contact with clothing, bedding, etc.; and they are largely unsuccessful for any long term use.

Reliable, permanent access to internal body locations could provide electrical power for heart assist pumps, for recharging implanted batteries, for implanted hearing devices, and for any other use where electrical energy is useful inside the animal or human body. Such a system could be adapted for hydraulic driving systems or for permanent connections for kidney dialysis, sensing devices, or any other helpful or experimental purposes in which one might want access to the body fluids or organs. Furthermore, with the advent of fiberoptics, inspection of internal body surfaces and monitoring of changes in internal body systems could be readily accomplished.

DISCLOSURE OF INVENTION

A subcutaneous body entry communication device and method for implanting and using same is described. The device operably interconnects an external medical device or other device to an internal body location of an animal having a tooth, the tooth having a crown section and a root section. The tooth crown section is exposed above an attached gingiva; the tooth root section is unexposed beneath a free gingiva and supported by a jaw.

The device includes a first communication pathway means implanted in or along the tooth that extends from the crown section, above the attached gingiva to the root section, beneath the free gingiva. A second communication pathway means is implanted in the jaw and operatively connected to the first communication pathway means. The second communication pathway means extends toward the internal body location to enable the medical device to communicate with the internal body location.

Installing the body entry communication device involves implanting the first communication pathway means in the tooth. The second communication pathway means is implanted in the jaw.

BRIEF DESCRIPTION OF THE DRAWINGS

Preferred embodiments of my invention are illustrated in the accompanying drawings, in which:

FIG. 1 is a sectional view of a first embodiment of the body entry communication device;

FIG. 2 is a cutaway view of the first embodiment of the body entry communication device;

DETAILED DESCRIPTION OF PREFERRED EMBODIMENTS

Figure 3:
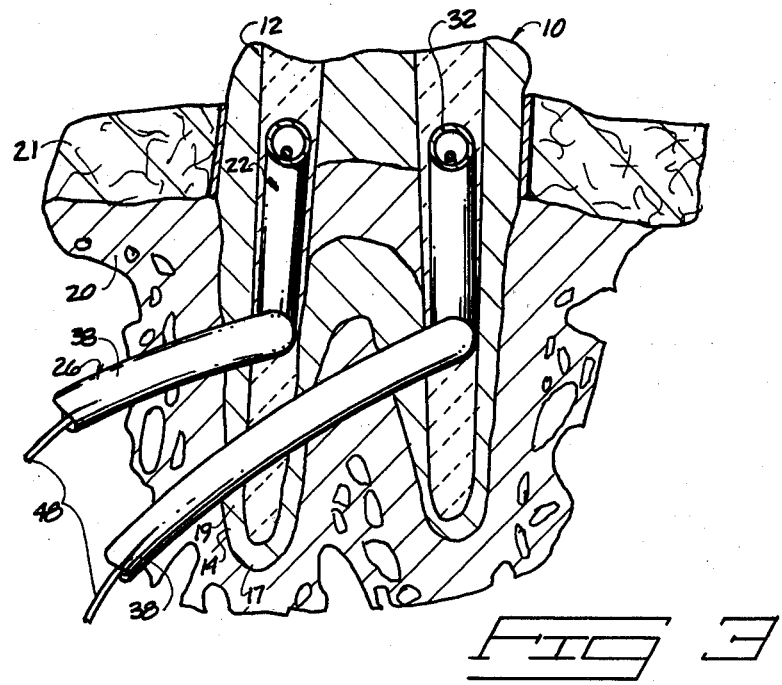
FIG. 3 is a sectional view of a second embodiment of the body entry communication device.

The present invention involves a subcutaneous body entry communication device. The device operatively interconnects an external medical device or other device with an internal body location. Thus, an interface to the outside world from within an animal or human body is provided.

Modern medical procedures and the ever-widening scope of man's knowledge about the biological aspects of his body have made a demand on the medical arts to provide new solutions to the problems thus created. Accessing the internal organs, tissues, and structures of the human body (as well as the bodies of other animals) has aided in the quest for understanding the body. Further benefits accrue from the ability of medical personnel and laboratory researchers to communicate to the internal systems and structures of the body in medical and experimental procedures.

The human body (as well as the bodies of animals) is designed to be self-sufficient. Nature has jealously guarded those secrets relating to the functioning of the body's internal mechanisms. Man's efforts to study these systems and mechanisms at work are frustrated by the very nature of the design being studied. Maintaining a communication pathway between the inside and the outside of the body runs contrary to the proper functioning of the body. Efforts to communicate the body interior systems and mechanisms have resulted in many unsatisfactory "jerry-rigged" interfaces. The problem is, the human body was just not designed for external connections. Neither is there an animal with physical characteristics that oblige this sort of inquiry.

Running connections through the skin is a substantially unsatisfactory technique of interfacing the body to the outside world. The connections move in the flesh creating sores and infections and thereby inviting disease, the contacts being made to the skin are not stable and are easily dislodged, and the scarring and visibility of the connections is cosmetically unappealing to a subject carrying such an interface on his body.

My invention is concerned with using the animal's tooth as a substitute for interfacing connections from the outside world to the animal's internal body locations.

The features of teeth are well understood by the scientific and medical arts and for the sake of this discussion the rudiments of dentistry are not included. Suffice it to say, for the purpose of discussion, the tooth 10 includes (as illustrated in FIGS. 1 through 5) a crown 12, a root 14, a root nerve 15, a root base 17, root pulp 19, a free gingiva 16 and an attached gingiva 18. Associated with a tooth 10 is a jaw 20 (FIG. 5) and gum tissue 21. For purposes of one embodiment of my invention, veins or arteries 11 (FIG. 5) are included in the discussion.

In its simplest embodiment (FIG. 6), the subcutaneous body entry communication device involves a first communication pathway means 22 and a second communication pathway means 26.

The first communication pathway means 22 contains either an electrically conductive material or a fluid conductive material. Alternatively, the pathway means 22 may contain a light conductive material.

The second communication pathway means 26 may be a conductor of electricity, such as a wire or a conductor of light, such as a fiberoptic strand; the second communication pathway means 26 may also be a fluid conductor.

Figure 4:
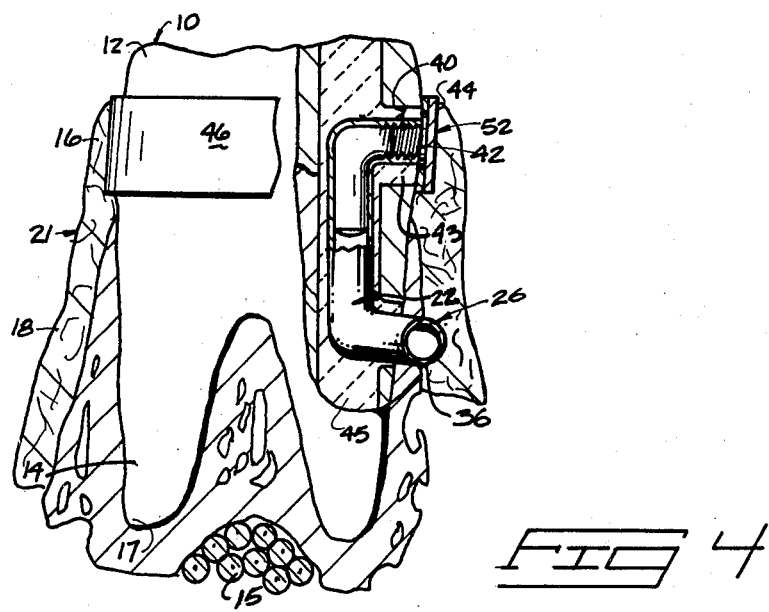
FIG. 4 is a cutaway view of a tooth showing a third embodiment of the body communication entry device.

Included in my invention is an interface point 50 between the first communication pathway means 22 and the outside world. The interface point 50 can be an electrical (or light) interface interconnecting means 32 (FIG. 1) or a fluid interface interconnecting means 40 (FIG. 4). The electrical interface 32 contains an electrode means 34 accessible by outside medical instruments or other instruments, such as recorders, power supplies, signal conditioners, etc.; the fluid interface 40 contains a fluid conductive means 42 for interfacing the internal body locations to external medical devices or other devices.

Plug means 44 (FIGS. 2 and 4) are provided for sealing the first communication pathway means 22 when access to internal body locations is not desired. The plug means is held in position by a securing band 46.

Figure 6:
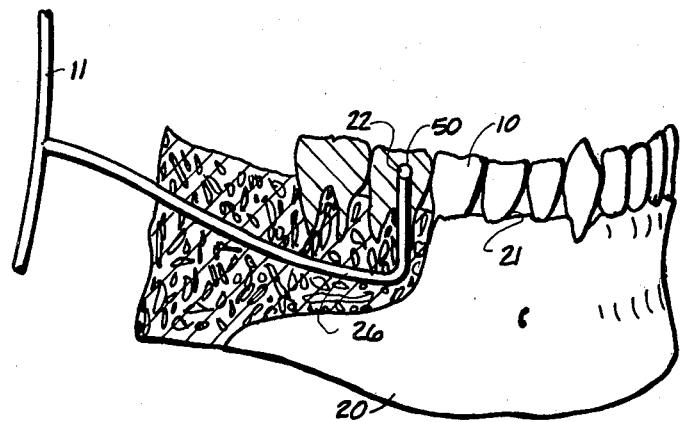
FIG. 6 is a cutaway view of the body communication entry device in the jaw.

A first embodiment of my invention (FIGS. 1 and 2) involves the placement of electrical (or light) conductors from an internal body location, along the jaw 20, and through the tooth 10 to the outside world. FIG. 6 is a general representation of the conductor placement. This first embodiment is useful for pacemaker and other heart assist devices, hearing aids, electrical body monitoring devices, and any other device requiring electric driving power or generating electrical signals. Such embodiment also lends itself to the placement of light conductors in the body. As fiberoptic technology advances, placement of light conductors in the body may provide visual monitoring of internal systems.

Interface with the outside world is made by performing one or more root canals on existing teeth 10. The tooth is excavated by drilling to form a root canal aperture 24 (FIGS. 1 and 2). The root pulp 19 is removed from the root base 17. The aperture 24 extends from the tooth crown 12 to the tooth root 14 from above the free gingiva 16 to below the point of attachment of the attached gingiva 18. The first communication pathway means 22 is implanted in the tooth extending from the crown section 12 above the attached gingiva 18 to the root section 14 beneath the free gingiva 16. The second communication pathway means 26 is implanted in the jaw 20 and operably interconnected with the first communication pathway means 22. The second communication pathway means 26 extends toward the internal body location being accessed. The electrical (or light) connectors 32 are placed inside the root canal aperture 24 with access either on a top or a side of the tooth used. Under the attached gingiva 18, access to the bottom of the root canal aperture 24 is surgically made and connection is made to the conductive material 28 inside the tooth. The canal is then cemented (filled) with a nonconductive filling composition 45. The conductive material 30 forming the second communication pathway means 26 extends from the bottom of the tooth 17 (root base) under the gum tissue 21 to the back of the jaw 20 (FIG. 6) and under the skin (not shown) to the desired location in the body.

The electrical conductive material 28 and 30 may be of the ribbon design to reduce perturbation of the gum tissue 21. The conductive material could be channeled underneath the teeth and above the central nerve 15 (FIG. 2) in the jaw 20. The nerve 15 could also be destroyed to allow access for larger conductive means. For side access to the tooth 10, the conductive means 28 and 30 could be laid in a channel cut into the jaw bone 20 to reduce stress on the thin gum tissue 21.

As an alternative, a plurality of conducting means (not shown) is run through the first and second communication pathways of each tooth excavated. Using microminiaturization techniques, a plurality of individual wires (or other conductive means) is contained in a single tooth entry. A microminiature connector (not shown) is used to interface the conductors to the outside world. One application for such an arrangement involves interfacing subcutaneous transducers (not shown) to an external hearing aid device (not shown) to allow deaf persons to hear.

A plug means 44 (FIG. 2) is part of an electrical interface interconnecting means 32. The plug means 44 may be made of a pliable nonconductive material to seal out water and to provide the conductive material 28 and 30 with electrical connections on the surface of the tooth 10. A securing band 46 is placed over the plug means 44 to tighten the electrical connection made to the tooth. The wires (not shown) connected to the tooth 10 are routed out of the mouth. The electrical interface connecting means 32 contains an electrode means 34 inserted through an electrode tooth aperture 35.

A second embodiment of my invention (FIG. 3) apprehends a problem arising with wire insulation and flexibility when in contact with body fluids. In this embodiment a conduit such as a fluid conductive material 38 is run from the interface interconnecting means 32 through the first communication pathway means 22 and through the second communication pathway means 26 to a body location such as a heart pump. The electrical conductive leads 48 are run through the conduit 38 to electrical contacts at the heart pump or other driven device to power the pump. While the leads 48 are connected to the electrical source, the tube 38 is purged with low pressure sterile air or gas to dry the tube and the electrical insulation. The electrical conductive material 48 can be made more flexible by using a woven mesh with total cross-sectional area adequate for the current requirements. An alternative form of this embodiment uses fluid conductive tubes 48 filled with a highly conductive liquid.

Figure 5:
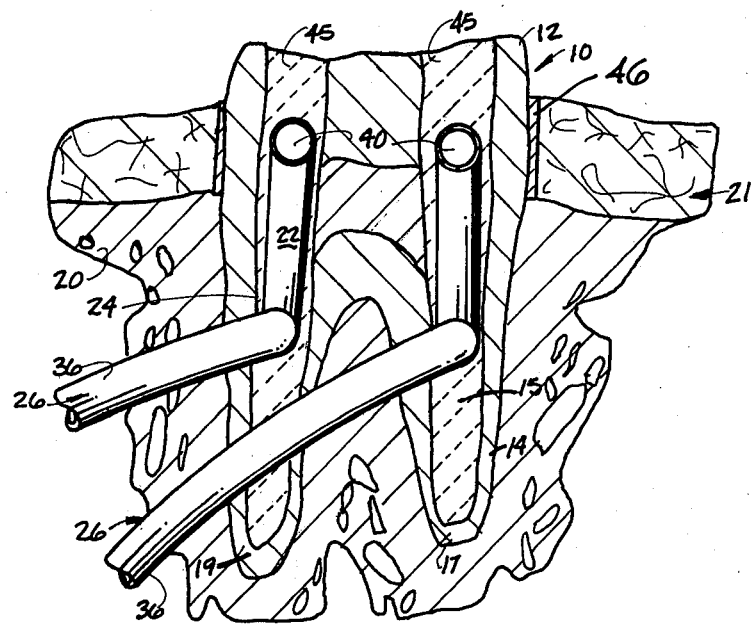
FIG. 5 is a sectional view of the third embodiment of the body entry communication device.

A third embodiment of my invention involves a fluid conductive material 36 (FIGS. 4 and 5). The tooth is excavated by drilling a root canal aperture 24 in a similar manner as for the first embodiment of my invention. The fluid conductive material 36 constitutes the first communication pathway means 22 and the second communication pathway means 26. A fluid interface interconnecting means 40 is provided containing a fluid conductive means 42 within a fluid means tooth aperture 43. The fluid conductive material 36 is secured in the tooth 10 by a filling compound 45. A metal tube 42 inside the tooth 10 with a sealing plug 44 and retaining band 46 are used. As an alternative, an active connector (not shown) to supply and return fluid through the tooth is configured as a band for attachment around the tooth. A sealing means 52 for the first communication pathway 22 is provided in this embodiment.

An application of the fluid system is in a kidney dialysis arrangement. The system includes fluid conductive material 36 such as hydraulic tubing which is connected to a nearby vein 11 (FIG 6). A second fluid conductive material is connected to an artery (not shown).

Another embodiment of this invention uses one or more tubes in communication with the abdominal cavity to inject and later remove saline-like solution to perform the same function of blood cleansing as kidney dialysis. The fluid embodiment of my invention is also useful as a sample system for collection of body fluid from specific locations.

Other combinations and embodiments of my invention are possible and, therefore, the scope of my invention should only be limited by that of the following claims.

I claim:

1. In a permanent subcutaneous body entry communication method for operatively interconnecting an external device with a predetermined internal body location of an animal having a tooth with a crown section exposed in a mouth cavity above an attached gingiva and a root section unexposed beneath a free gingiva and supported by a jaw, the method comprising:
   forming an opening in the tooth along the crown section thereof above the attached gingiva;
   implanting a first communication pathway means in the tooth that extends from an interface point at the opening in the crown section above the attached gingiva to the root section beneath the free gingiva; the interface point being adapted to physically connect the first communication pathway means to the external device;
   implanting a second communication pathway means in the jaw that is operably interconnected to the first communication pathway means and operatively extending subcutaneously toward the predetermined internal body location without intersecting the gingiva.

2. The subcutaneous body entry communication method as defined in claim 1 wherein the tooth has a root nerve in a base of the root section and wherein the first communication pathway means is formed at least in part by drilling a root canal aperture in the tooth with at least a portion of the root canal aperture forming at least a portion of the first communication pathway means.

3. The subcutaneous body entry communication method as defined in claim 1 wherein the first and second communication pathway means are electrically conductive for transmission of electrical energy therealong to enable the device to communicate with the internal body location.

4. The subcutaneous body entry communication method as defined in claim 1 wherein the first and second communication pathway means are fluid conductive for transmission of a fluid therealong to enable the device to communicate with the internal body location.

5. The subcutaneous body entry communication method as defined in claim 1 wherein the first and second communication pathway means are light conductive for transmission of light therealong to enable the device to communicate with the internal body location.

6. The subcutaneous body entry communication method as defined in claim 3 wherein the first communication pathway means is formed of electrically conductive material extending internally through the tooth between the crown section and the root section.

7. In the subcutaneous body entry communication method as defined in claim 6 wherein an interface interconnecting means is provided at the interface point by installing an electrode means in the tooth above the attached gingiva, said electrode means being operably interconnected to the first communication pathway means.

8. The subcutaneous body entry communication method as defined in claim 7 wherein the electrode means is installed by drilling an aperture in the tooth above the attached gingiva and inserting the electrode into the aperture in operative communication with the first communication pathway means.

9. The subcutaneous body entry communication method as defined in claim 4 wherein the first communication pathway means is formed of fluid conductive material extending internally through the tooth between the crown section and the root section.

10. In the subcutaneous body entry communication method as defined in claim 9 wherein an interface interconnecting means is provided at the interface point by installing a fluid conductive means in the tooth above the attached gingiva, said fluid conductive means being operatively interconnected to the first communication pathway means.

11. The subcutaneous body entry communication method as defined in claim 10 wherein the interface interconnecting means is installed by drilling an aperture in the tooth above the attached gingiva and inserting the fluid conductive means into the aperture in operative communication with the first communication pathway means.

12. The subcutaneous body entry communication method as defined in claim 5 wherein the first communication pathway means is formed of light conductive material extending internally through the tooth between the crown section and the root section.

13. In the subcutaneous body entry communication method as defined in claim 12 wherein an interface interconnecting means is provided at the interface point by installing a light conducting means is the tooth above the attached gingiva, said light conducting means being operatively interconnected to the first communication pathway means.

14. The subcutaneous body entry communication method as defined in claim 13 wherein the interface interconnecting means is installed by drilling an aperture in the tooth above the attached gingiva and inserting the light conductive means into the aperture in operative communication with the first communication pathway means.

15. A permanent subcutaneous body entry communication device for operatively interconnecting an external medical device with a predetermined internal body location of an animal having a tooth with a crown section exposed in a mouth cavity above an attached gingiva and a root section unexposed beneath a free gingiva and supported by a jaw, comprising:
   a first communication pathway means implanted in the tooth and extending from the crown section above the attached gingiva to the root section beneath the free gingiva;
   interface means operatively connected to the pathway means and mounted to the tooth along the crown section thereof, above the attached gingiva, for connection to an external device; and
   a second communication pathway means implanted in the jaw operatively connected to the first communication pathway means and extending subcutaneously toward the internal body location without intersecting the gingiva to enable the medical device to communicate with the predetermined internal body location.

16. A subcutaneous body entry communication device as defined in claim 15 wherein the first and second communication pathway means are electrically conductive for transmission of electrical energy therealong.

17. A subcutaneous body entry communication device as defined in claim 15 wherein the first and second communication pathway means are fluid conductive for transmission of a fluid therealong.

18. A subcutaneous body entry communication device as defined in claim 15 wherein the first and second communication pathway means are light conductive for transmission of light therealong.

19. A subcutaneous body entry communication device as defined in claim 16 wherein the first communication pathway means is formed of electrically conductive material extending internally through the tooth between the crown section and the root section.

20. A subcutaneous body entry communication device as defined in claim 19 wherein the interface means comprises an electrode means adapted for installation in the tooth above the attached gingiva, said electrode means being operatively interconnected to the first communication pathway means.

21. A subcutaneous body entry communication device as defined in claim 20 wherein the electrode means is installed in an aperture in the tooth above the attached gingiva and the electrode is in operative communication with the first communication pathway means.

22. A subcutaneous body entry communication device as defined in claim 17 wherein the first communication pathway means is formed of fluid conductive material extending internally through the tooth between the crown section and the root section.

23. A subcutaneous body entry communication device as defined in claim 22 wherein the interface means is comprised of:
a fluid conducting means adapted to be situated within an aperture in the tooth above the attached gingiva, said fluid connecting means being operatively interconnected to the first communication pathway means.

24. A subcutaneous body entry communication device as defined in claim 18 wherein the first communication pathway means is formed of light conductive material extending internally through the tooth between the crown section and the root section.

25. A subcutaneous body entry communication device as defined in claim 24 wherein the interface means is comprised of:
a light conducting means adapted to be received in an aperture in the tooth above the attached gingiva, said light conducting means being operatively interconnected to the first communication pathway means.

26. A subcutaneous body entry communication device as defined in claim 15, further comprising:
a plug means at an outer tooth surface above the attached gingiva for sealing the first communication pathway means and interface means against entry from outside the body.

27. A subcutaneous body entry communication device as defined in claim 26, further comprising:
a securing band to hold the plug means in position.

28. A subcutaneous body entry communication device as defined in claim 16, wherein the first and second communication pathway means include a plurality of electrical conductors.

29. A subcutaneous body entry communication device as defined in claim 21 wherein the electrode means provides a plurality of electrical connections.

30. A permanent subcutaneous communication interface for an animal having a tooth with an exposed external crown section extending into a mouth cavity externally of an attached gingiva, and a root section extending subcutaneously beneath the attached gingiva and supported by a jaw, said interface comprising:
pathway means implanted within the tooth and the jaw, extending therein from the crown section through the root section inwardly of the attached gingiva and through the jaw without intersecting the gingiva;
a connector adapted to be mounted in a tooth along an exposed crown section thereof, externally of the attached gingiva, operably connected to the pathway means; and
plug means releasably secured to the connector for selectively sealing the connector and pathway means from the environment external to an associated tooth.

* * * * *